United States Patent
Green et al.

(10) Patent No.: US 11,400,070 B2
(45) Date of Patent: Aug. 2, 2022

(54) METHODS OF TREATING RETINAL DISEASES

(71) Applicants: Alimera Sciences, Inc., Alpharetta, GA (US); The Johns Hopkins University, Baltimore, MD (US)

(72) Inventors: Kenneth E. Green, Johns Creek, GA (US); Peter Campochiaro, Baltimore, MD (US); Yogita Kanan, Baltimore, MD (US)

(73) Assignees: Alimera Sciences, Inc., Alpharetta, GA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/401,385

(22) Filed: May 2, 2019

(65) Prior Publication Data

US 2019/0336466 A1    Nov. 7, 2019

Related U.S. Application Data

(60) Provisional application No. 62/666,379, filed on May 3, 2018.

(51) Int. Cl.
*A61K 31/25* (2006.01)
*A61K 9/00* (2006.01)
*A61P 27/02* (2006.01)

(52) U.S. Cl.
CPC ............ *A61K 31/25* (2013.01); *A61K 9/0051* (2013.01); *A61P 27/02* (2018.01)

(58) Field of Classification Search
CPC ........ A61K 31/25; A61K 9/0051; A61P 27/02
See application file for complete search history.

(56) References Cited

U.S. PATENT DOCUMENTS

| | | | | |
|---|---|---|---|---|
| 8,470,784 B2* | 6/2013 | Liu | ......................... | A61K 45/06 514/20.8 |
| 9,549,963 B2* | 1/2017 | Liu | ......................... | A61K 38/07 |
| 2006/0199868 A1* | 9/2006 | Collier | ................. | A61K 31/138 514/651 |
| 2010/0204137 A1* | 8/2010 | Russ | ....................... | A61K 38/06 514/2.3 |
| 2011/0021526 A1* | 1/2011 | Deshpande | .......... | A61K 31/215 514/236.2 |
| 2011/0177047 A1* | 7/2011 | Liu | ......................... | A61K 38/06 424/94.1 |
| 2013/0046382 A1* | 2/2013 | Mazzocchi | ........... | A61F 9/0017 623/6.63 |
| 2013/0142733 A1* | 6/2013 | Harth | ................... | A61K 9/5153 424/9.6 |
| 2013/0236526 A1 | 9/2013 | Huang et al. | | |
| 2013/0303473 A1* | 11/2013 | Wilson | ............... | A61K 31/7048 514/29 |
| 2014/0044689 A1* | 2/2014 | Liu | ........................ | A61K 38/07 424/94.1 |
| 2016/0058825 A1* | 3/2016 | Liu | ........................ | A61K 38/07 424/94.1 |
| 2017/0105873 A1* | 4/2017 | Mazzocchi | ......... | A61F 9/00727 |
| 2017/0326197 A1* | 11/2017 | Liu | ........................ | A61K 38/07 |

OTHER PUBLICATIONS

Heckenlively et al. Clinical findings and common symptoms in retinitis pigmentosa. Am J Ophthalmol. 1988, 105(5):504-511. (Year: 1988).*

Greenstein et al. Effects of early diabetic retinopathy on rod system sensitivity. Optom Vis sci, Jan. 1993;70(1):18-23. (Year: 1993).*

Cho et al. Selective loss of S-cones in diabetic retinopathy. Arch Ophthalmol. 2000, 118:1393-4000 (retreated from https://jamanetwork.com/journals/jamaophthalmology/fullarticle/413723). (Year: 2000).*

Osborne, NN et al., "Metipranolol Blunts Nitric Oxide-Induced Lipid Peroxidation and Death of Retinal Photoreceptors: A Comparison with Other Anti-Glaucoma Drugs", Investigative Ophthalmology and Visual Sciences, Oct. 2004, vol. 45, No. 10, pp. 3787-3795.

Kowluru, R. et al., "Oxidative Stress and Diabetic Retinopathy", Experimental Diabetes Research, 2007, vol. 2007, No. 43603, pp. 1-12.

Osborne, NN et al., The Beta-Adrenergic Receptor Antagonist Metipranolol Blunts Zinc-Induced Photoreceptor and RPE Apoptosis, Investigative Ophthalmology and Visual Sciences, Jul. 2006, vol. 47, No. 7, pp. 3178-3186.

Kanan, Y et al., Metipranolol Promotes Structure and Function of Retinal Photoreceptors in the rd10 Mouse Model of Human Retinitis Pigmentosa, Journal of Neurochemistry, Dec. 2018, vol. 148, No. 2, pp. 307-318.

International Search Report for Application No. PCT/US2019/030337 dated Jul. 10, 2019.

* cited by examiner

*Primary Examiner* — Robert A Wax
*Assistant Examiner* — Olga V. Tcherkasskaya
(74) *Attorney, Agent, or Firm* — Crowell & Moring LLP

(57) ABSTRACT

A method of treating or inhibiting degeneration of a retina of a subject in need thereof comprising administering an effective amount of a compound of metipranolol, or a metabolite thereof, to an organ, a tissue, or the subject, wherein the degeneration of the retina is caused by an ocular disease. In some embodiments, the compound, or a metabolite thereof, is administered topically, orally, or parenterally. In some embodiments, a drug delivery vehicle comprising a dosage of the compound, or the metabolite of, is delivered parenterally via intravitreal injection. In further embodiments, the dosage may range from 0.5 μg/day-15 μg/day.

12 Claims, 16 Drawing Sheets

METHODS OF TREATING RETINAL DISEASES

RELATED APPLICATIONS

The present patent document claims the benefit of the filing date under 35 U.S.C. § 119(e) of Provisional U.S. Patent Application Ser. No. 62/666,379, filed May 3, 2018, which is hereby incorporated by reference.

BACKGROUND

An ocular condition can include an inflammatory, neoplastic, infectious, vascular, neovascular and/or degenerative disease, aliment or condition which affects or involves the eye or one of the parts or regions of the eye. Diseases of the retina, including age-related macular degeneration (AMD), retinitis pigmentosa (RP), and diabetic retinopathy (DR), are major causes of legal blindness in the United States. One disease that may lead to the development of an ocular condition affecting the retina is diabetes mellitus.

Diabetes mellitus, and its systemic and ophthalmic complications, represent an enormous public health threat in the United States. According to the CDC, more than 30 million people in the United States have been diagnosed with diabetes. All patients with diabetes are at risk of developing some form of diabetic retinopathy, an ophthalmic complication of diabetes that presents with symptoms including the swelling and leakage of blood vessels within the retina or the abnormal growth of new blood vessels on the surface of the retina. Diabetic retinopathy is a major complication of diabetes mellitus and a leading cause of visual impairment and blindness in the United States. Aiello L M., *Perspectives on diabetic retinopathy. Am J Ophthalmol.* 2003; 136:122-135.

Diabetic Macular Edema (DME), the primary cause of vision loss associated with diabetic retinopathy, is a disease affecting the macula, the part of the retina responsible for central vision. When the blood vessel leakage of diabetic retinopathy causes swelling in the macula, the condition is called DME. The onset of DME is painless and may go undetected by the patient until it manifests with the blurring of central vision or acute vision loss. The severity of this blurring may range from mild to profound loss of vision. As the population of diabetics increases, it is expected that the annual incidence of diagnosed DME will increase.

In diabetic retinopathy, visual loss is often secondary to disruption of the blood-retina barrier and the development of macular edema. Aiello L M., *Perspectives on diabetic retinopathy. Am J Ophthalmol.* 2003; 136:122-135. The retinal pigment epithelium (RPE) and blood vessels of the inner retina form the outer and inner blood-retina barriers. These barriers control the movement of fluid and solutes into the extracellular spaces of the neural retina. See Mäepea O., *Pressures in the anterior ciliary arteries, choroidal veins and choriocapillaris, Exp Eye Res.* 1992; 54:731-736. The RPE barrier is the pigmented cell layer just outside the neurosensory retina that nourishes retinal visual cells and comprises facilitated and active transporters, adherent junctions, and tight junctions. Although RPE function is essential to maintaining a dehydrated neural retinal environment, the regulation of the RPE barrier in macular edema has received relatively limited attention.

Another ocular condition affecting the retina is retinitis pigmentosa. As provided by the National Institutes of Health, retinitis pigmentosa ("RP") is a group of genetic diseases that occur in 1 out of 4000 people worldwide in which one of many different mutations causes rod photoreceptor cell death resulting in night blindness. With so many different pathogenic mutations, it appears that there are many different mechanisms by which rod cell death occurs. Regardless of the mutation and the mechanism of rod cell death, after rods die, cone photoreceptors undergo gradual degeneration resulting in gradual constriction of visual fields and eventual blindness.

A further ocular condition affecting the retina is choroidal neovascularization ("CNV"). CNV is the creation of new blood vessels in the choroid layer underneath the retina. CNV can create a sudden deterioration of central vision, along with other symptoms including color disturbances and metamorphopsia when CNV breaks through the RPE to the subretinal space. Under these circumstances, vision loss may be rapid and severe.

In light of the above, a need exists for an effective treatment for ophthalmic complications of the retina to inhibit degeneration.

BRIEF SUMMARY

In one aspect of the present invention, a method of treating or inhibiting degeneration of a retina of a subject in need thereof comprising administering an effective amount of a compound of metipranolol, or a metabolite thereof, to an organ, a tissue, or the subject, wherein the degeneration of the retina is caused by an ocular disease selected from the group consisting of diabetic retinopathy, choroidal neovascularization, and retinitis pigmentosa. In some embodiments, the compound, or a metabolite thereof, is administered topically, orally, or parenterally. In some embodiments, a drug delivery vehicle comprising a dosage of the compound, or the metabolite of, is delivered parenterally via intravitreal injection. In further embodiments, the dosage may range from 0.5 µg/day-15 µg/day.

In further embodiments, wherein the compound, or a metabolite thereof, reduces suppresses deterioration of outer nerve layer. In other embodiments, the compound, or a metabolite thereof, reduces incidences of rod photoreceptor dystrophy. In still further embodiments, the compound, or a metabolite thereof, reduces incidences of cone photoreceptor dystrophy. In additional embodiments, the compound, or a metabolite thereof, suppresses the activation of the receptor for advanced glycation end products on retinal pigment epithelium cells.

In another aspect of the invention, a method of administering an effective amount of a compound of metipranolol, or a metabolite thereof, for treatment of an ocular condition affecting the health of a retina of a subject comprising injecting an effective amount of the metipranolol, or a metabolite thereof, into an organ, a tissue, or the subject, wherein the ocular condition is selected from the group consisting of diabetic retinopathy, choroidal neovascularization, and retinitis pigmentosa.

In still another aspect of the invention, method of treating or inhibiting dystrophy of rods and cones of a retina of a subject in need thereof comprising administering an effective amount of a compound of metipranolol, or a metabolite thereof, to an organ, a tissue, or the subject.

DETAILED DESCRIPTION OF THE DRAWINGS AND THE PRESENTLY PREFERRED EMBODIMENTS

Figure 1:
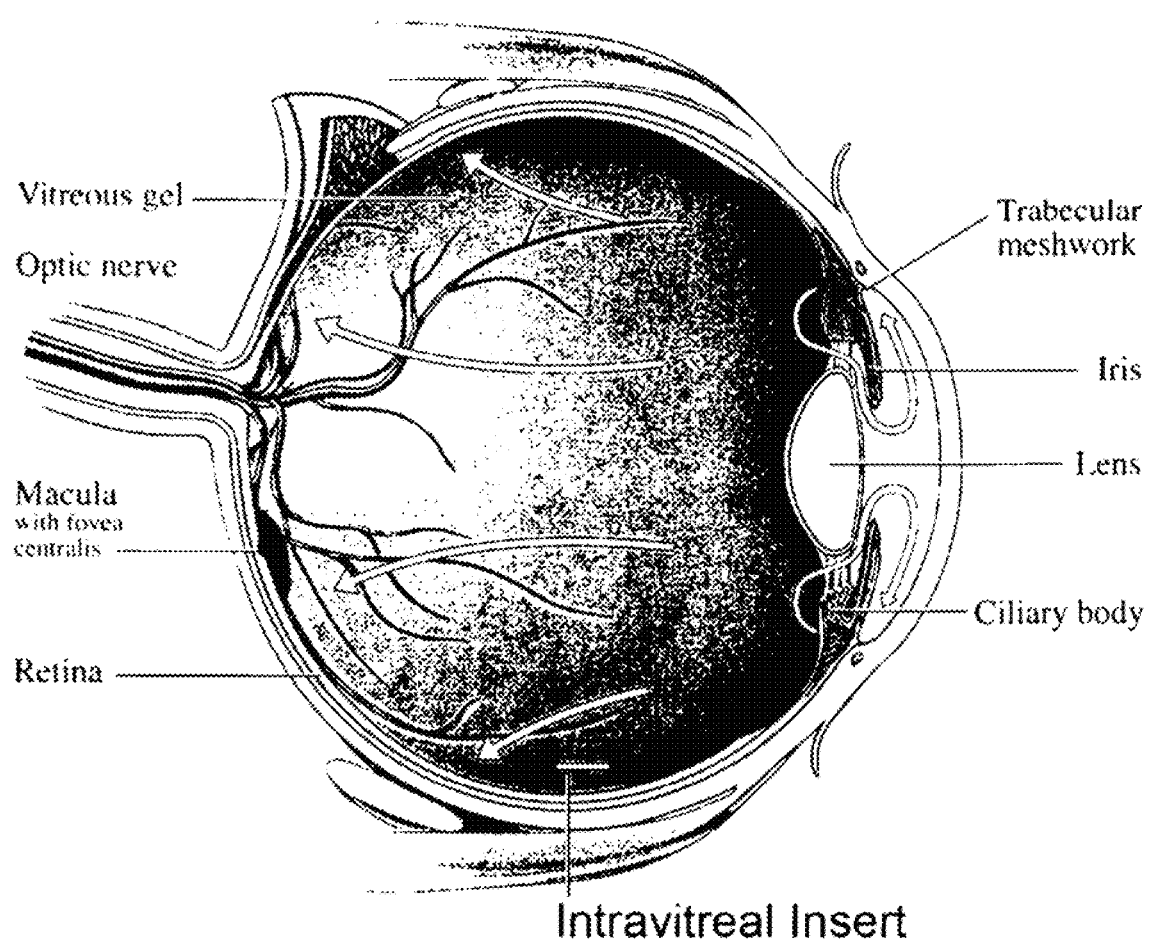
FIG. 1 is a schematic cross-sectional representation of the eye.

As used herein, each of the following terms has the meaning associated with it in this section.

"Ocular region" or "ocular site" means any area of the ocular globe (eyeball), including the anterior and posterior chamber and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include, but are not limited to, the anterior chamber, the posterior chamber, the vitreous cavity, the choroid, the suprachoroidal space, the conjunctiva, the subconjunctival space, the episcieral space, the intracorneal space, the subretinal space, sub-Tenon's space, the epicorneal space, the sclera, the pars plana, surgically-induced avascular regions, the macula, and the retina.

"Ocular condition" or "ocular disease" means a disease, ailment or condition which affects or involves the eye or one of the parts or regions of the eye. Broadly speaking, the eye includes the eyeball, including the cornea, and other tissues and fluids which constitute the eyeball, the periocular muscles (such as the oblique and rectus muscles) and the portion of the optic nerve which is within or adjacent to the eyeball.

"Injury" or "damage" are interchangeable and refer to the cellular and morphological manifestations and symptoms resulting from an inflammatory-mediated condition, such as, for example, inflammation, as well as tissue injuries caused by means other than inflammation, such as chemical injury, including chemical burns, as well as injuries caused by infections, including but not limited to, bacterial, viral, or fungal infections.

"Intraocular" means within or under an ocular tissue. An intraocular administration of a drug delivery system includes administration of the drug delivery system to a sub-tenon, subconjunctival, suprachoroidal, subretinal, intravitreal, anterior chamber, and the like location. An intraocular administration of a drug delivery system excludes administration of the drug delivery system to a topical, systemic, intramuscular, subcutaneous, intraperitoneal, and the like location.

"Choroidal neovascularization" (CNV) refers to the abnormal development, proliferation, and/or growth of blood vessels in the choroid which may break through the RPE and lie beneath the retina.

"Retina" refers to the innermost layer of the ocular globe surrounding the vitreous body and continuous posteriorly with the optic nerve. The retina is composed of layers including the: 1) internal limiting membrane; 2) nerve fiber layer; 3) layer of ganglion cells; 4) inner plexiform layer; 5) inner nuclear layer; 6) outer plexiform layer; 7) outer nuclear layer; 8) external limiting membrane; 9) a layer of rods and cones and the 10) retinal pigment epithelium (RPE).

"Retinal degeneration" refers to any hereditary or acquired degeneration of the retina and/or retinal pigment epithelium. Non-limiting examples include retinitis pigmentosa, Best's Disease, RPE pattern dystrophies, and age-related macular degeneration.

As used herein, a "therapeutically effective amount" is the amount of an agent which is sufficient to provide a beneficial effect to the subject to which the agent is administered.

The present invention relates in general to therapeutic methods for the treatment or inhibition of ocular conditions affecting the retina of a subject and more particularly to methods of treatment or inhibition of ocular conditions affecting the retina of a subject by the application of metipranolol, or a metabolite thereof. Metipranolol is a beta adrenoceptor receptor antagonist, also known as beta-blockers. Beta blockers are a mainstay and a first therapy choice for ocular diseases such as glaucoma. The available beta-blockers are typically categorized as being either nonselective (also referred to as "nonspecific"), inhibiting both $\beta1$ and $\beta2$-adrenoceptors, or $\beta1$ selective, which means that $\beta1$-adrenoceptors are preferably inhibited. In addition to their classical pharmacological actions $\beta$-blockers have also been shown to block $Na^+$ and $Ca^+$ channels, and act as antioxidants. See Osborne N N, Wood J P M, Chidlow G., *Neuroprotective Properties of Certain β-Adrenoceptor Antagonists Used for the Treatment of Glaucoma. J Ocular Pharmacol Ther.* 2005; 21(3): 175-181. Exemplary nonselective beta adrenergic receptor agonists and metabolites thereof include, but are not limited to, metipranolol and desacetylmetipranolol. The present invention provides novel, valuable, and surprising applications and uses for substances in the methods of the present invention. In particular, metipranolol and desacetylmetipranolol have demonstrated a range of pharmacological actions that have the potential to treat various ocular conditions, including diabetic retinopathy, retinitis pigmentosa, and choroidal neovascularization. It is believed that one of the non-classical actions (i.e. serving as an antioxidant) has an effect in treating these ocular diseases.

The active substance of the instant invention may be administered orally, topically, and parenterally, in dosage unit formulations containing conventional non-toxic pharmaceutically acceptable carriers. For oral administration in the form of a tablet or capsule, the active substance may be combined with nontoxic, excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

For topical administration, active substance can be incorporated into various types of ophthalmic formulations for topical delivery to the eye. They may be combined with ophthalmologically acceptable preservatives, surfactants, viscosity enhancers, penetration enhancers, buffers, sodium chloride, and water to form aqueous, sterile ophthalmic suspensions or solutions. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solutions may contain a thickener, such as, hydroxymethylcellulose, hydroxyethylcellulose, hydroxypropylmethylcellulose, methylcellulose, polyvinyl-pyrrolidone, or the like, to improve the retention of the formulation on the eye and thereby facilitate absorption into the inside of the eye.

Embodiments of the invention may be delivered parenterally, i.e., by intraocular, intravitreal, or subcutaneous (s.c.), by direct injection. In some embodiments, it will be understood by one of ordinary skill in the art that generally, dosage ranges may be determined based on the method of application of the beta adrenergic receptor antagonists of the present invention. In one aspect, suitable dosage ranges include 1-1000 milligrams daily, alternately 10-500 milligrams daily, and optionally 50-500 milligrams daily, depending as usual upon the exact mode of administration, form in which administered, the indication toward which the administration is directed, the subject involved and the body weight of the subject involved, and the preference and experience of the physician in charge.

The active ingredient may be delivered in a number of drug delivery vehicles. In some embodiments, the active pharmaceutical ingredient may be delivered to the ocular region through a drug delivery vehicle, such as an intravitreal insert, or intraocular delivery system which may or may not be bioerodible. The intravitreal insert delivers sustained sub-microgram levels of a beta adrenoceptor receptor antagonist to the eye. The intravitreal insert may have a relatively high dosage or a relatively low dosage. The intravitreal insert can be configured to deliver a therapeutic effect for variable durations. For example, the dosage duration may be at least 3 months, 6 months, 12 months, at least 18 months, at least 24 months, at least 30 months and/or at least 36 months.

The intravitreal insert can provide sustained delivery of sub-microgram levels of metipranolol or desacetylmetipranolol over time. For example, in some embodiments, the intravitreal insert may deliver at least 0.5 µg per day-15 µg per day for a dosage duration of at least 3-12 months, at least 24 months, and/or at least 36 months. In other exemplary embodiments, the low-dose intravitreal insert may deliver at least 0.5 µg per day, at least 0.75 µg per day, at least 1 µg per day, or at least 2 µg per day for a dosage duration of at least 3 months, 6 months, at least 12 months, at least 24 months, and/or at least 36 months.

The intravitreal insert may be inserted into the eye using a conventional ocular insertion device. For example, the intravitreal insert may be inserted using a device with a 25, 27 or 30-gauge needle. Typically, the insertion procedure is non-surgical and may be performed in a retinal specialist's office. For insertion, the needle of the device is inserted into the eye through the pars plana. The needle is inserted to about the equator of the eye and then the plunger of the device is depressed such that the intravitreal insert or intraocular delivery system is inserted into the vitreous of the eye. After injection, the insert or delivery system settles inferiorly at the posterior portion of the eye (distal the pars plana) at or near the vitreous base of the eye or generally in a region of the posterior segment that is outside of the visual axis. FIG. 1 is a schematic cross-sectional representation of the eye. FIG. 1 provides an illustration of the location of an insert in the eye which might be one delivery option. In different embodiments, the intravitreal insert may be positioned in alternative locations and be of different forms including an amorphous mass which may or may not bio-erode.

The embodiments of the present invention may be helpful in treating or inhibiting degradation of the retina of a subject in need. One such disease that effects the retina is diabetic retinopathy. Diabetic retinopathy is a microvascular complication of diabetes mellitus. Diabetic retinopathy is a disease in which damage occurs to the retina due to high blood sugar levels. Blood vessels may swell, leak, or close, which stops blood from passing through. Leaking of the blood vessels may cause swelling of the retina including the macula. Swelling of the macula is defined as diabetic macular edema. Diabetic retinopathy may also lead to the deterioration of other parts of the retina including the retinal pigment epithelium, or RPE. RPE lies between the choroid and neurosensory retina to form the blood-retinal barrier. RPE serves an important barrier to maintain retinal health and include a collection of interrelated structures and activities that regulate the transepithelial movement of solutes, including: diffusion through the paracellular spaces, facilitated diffusion through the cells, active transport, receptor-mediated and bulk phase transcytosis, and metabolic processing of solutes in transit. RPE function is essential to maintaining a dehydrated neural retinal.

The accumulation of advanced glycation end products (AGE) is a consequence of hyperglycemia in diabetic patients. AGEs arise primarily by the modification of amine groups of proteins by reactive dicarbonyls. While not being held to theory, the progression of diabetic retinopathy may be associated with the accumulation of AGE in the retina and vitreous. See Kakehashi A, Inoda S, Mameuda C, Kuroki M, Jono T, Nagai R, Horiuchi S, Kawakami M Kanazawa Y. (2008) *Relationship among VEGF, VEGF receptor, AGEs, and macrophages in proliferative diabetic retinopathy. Diabetes Res Clin Pract.* 2008; 79: 438-445. The receptor for advanced glycation end products (RAGE) is primarily expressed on the apical surface of the RPE. Surprisingly, it has been demonstrated that the metipranolol, and its metabolite, desacetylmetipranolol suppresses the activation of RAGE, which limits the deterioration of RPE.

Metipranolol is a β-blocker used in the treatment of ocular hypertension. Desacetylmetipranolol is the principal metabolite of metipranolol and is also active as a β-blocker. Surprisingly, it is been found that by inhibiting or suppressing activation of RAGE helps to prevent the degeneration of RPE. The suppression of RAGE activation by metipranolol and desacetylmetipranolol in the current studies would not appear to be related to their ability to antagonize β adrenergic receptors.

Embodiments of the present invention may also be helpful with treating and inhibiting degeneration of the retina of a subject in need where the patient is suffering from retinitis pigmentosa and/or choroidal neovascularization. Retinitis pigmentosa is a group of diseases in which one of many different mutations causes rod photoreceptor cell death resulting in night blindness. With so many different pathogenic mutations, it appears that there are many different mechanisms by which rod cell death occurs. Regardless of the mutation and the mechanism of rod cell death, after rods die, cone photoreceptors undergo gradual degeneration resulting in gradual constriction of visual fields and eventual blindness. Surprisingly, it has been found that metipranolol and desacetylmetipranolol promotes rod and cone photoreceptor survival and function. It has also been found that metipranolol and desacetylmetipranolol suppress the development of choroidal neovascularization. While not being held to theory, as will be discussed by the Examples, metipranolol and desacetylmetipranolol reduce nitrates and 3-nitrotyrosine content indicating that they block peroxynitrite-induced nitrosative damage as well as blocking superoxide production potentially via NADPH oxidase.

The intravitreal insert may comprise biocompatible polymers or copolymers which may or may not also be bioerodible including, but not limited to, Dexon, Vicryl, Polysorb, poly(lactide-coglycolide) (PLGA), polyglycolic acid (PGA), polylactic acid (PLA), polycaprolactone (PCL), polydioxanone (PDO), polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, polyvinyl acetates, plasticized ethylene vinylacetate copolymer, polyvinyl alcohol, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4-isopropylidene diphenylene carbonate), vinylidene chloride, acrylonitrile copolymer, vinyl-chloride-diethyl fumerate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer, vinylidene chloride-acrylonitrile copolymer, etc. In preferred embodiments, the intravitreal insert comprises such as poly(lactic-co-glycolic acid). In alternative embodiments, the intravitreal insert may form from a non polymeric matrix.

EXAMPLES

Example 1

A study was performed to evaluate if metipranolol and desacetylmetipranolol compounds can reverse the RPE barrier dysfunction induced by the administration of an AGE compound, glycated human serum albumin (gHSA). ARPE-19/HPV-16 cell line was obtained from The American Type Culture Collections, Manassas, Va. The ARPE-19 cells were cultured on permeable-membrane inserts (Costar Clear Transwell, 0.4 μm pore) containing DMEM/F12/HAM with 10% fetal bovine serum (FBS), 1.2 g/L sodium bicarbonate, and 10 mL/L L-glutamine-penicillin-streptomycin in a humidified incubator and kept at 37° C. in 5% CO2. After the cells attached, the medium was modified to contain only 1% FBS, and changed every 2 to 3 days. Barrier properties of confluent monolayers were assessed by measuring transepithelial electrical resistance (TEER) using an epithelial volt-ohmmeter (WPI, Sarasota, Fla.) equipped with an STX2 electrode (WPI).

Resistance measurements for individual wells were determined from four measurements, and corrected for the inherent transwell resistance. For each condition, at least three independent resistant measurements from separate transwell cultures were performed and the mean±SE calculated. Concentration-response curves were analyzed by nonlinear regression analysis (Prism; GraphPad Software, Inc., San Diego, Calif.). The ED50 were entered as variables in the dose-response equation and reported as best-fit values. Starting values for the regression analyses were determined by visual inspection of the data.

Cytotoxicity of test compounds was assessed by microscopic inspection of cellular monolayers and reductions in TEER following the administration of test compounds. All compounds were formulated fresh on the day of the experiment. Final concentrations were prepared by serial dilutions in DMEM media. Separate vehicle controls were prepared for each study. Formulation for all agents utilized vehicles containing less than 0.1% DMSO. Previous studies have shown that DMSO at a concentration of 0.1% or less does not alter the TEER of the RPE over the 6-hour study period used in these experiments.

Table 1 describes the concentration-response parameters for the compounds in ARPE-19 assay.

TABLE 1

| Compound | EC50 (μmol/L) | Hill coefficient | Cytotoxic |
| --- | --- | --- | --- |
| Desacetylmetipranolol | 0.98 | 1 | No |
| Metipranolol | 1.3 | 1 | No |
| Fluocinolone | — | — | No |

Results

Figure 2:
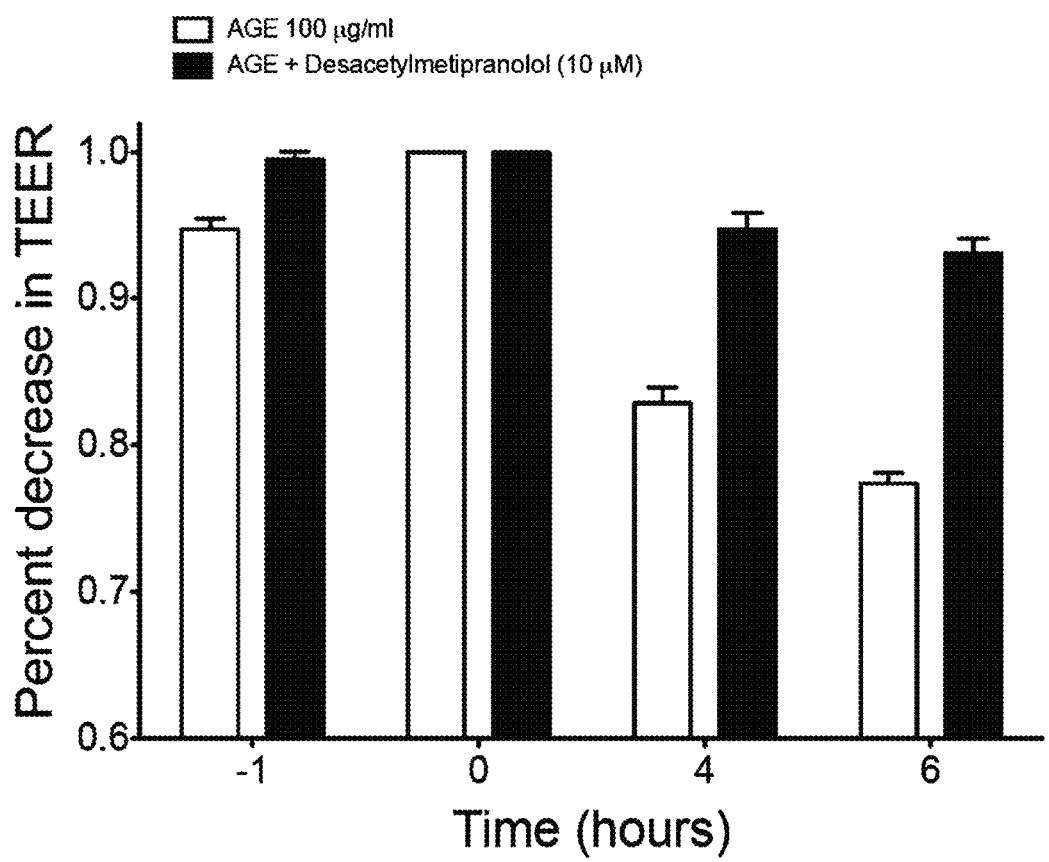
FIG. 2 is a graph showing percent decrease in TEER for APRE-19 monolayers over a period of time.

As shown in FIG. 2, administration of 100 μg/mL of gHSA to confluent ARPE-19 monolayers produced a significant drop in TEER. These responses were time-dependent with maximum reduction in resistance of 23±1.7% measured at 6 hours. FIG. 2 also shows the change in TEER at 4 and 6 hours following gHSA administration alone in cultures that had been pretreated with desacetylmetipranolol (10 μM). Pretreatment with desacetylmetipranolol suppressed the gHSA induced reduction in RPE resistance.

Figure 3:
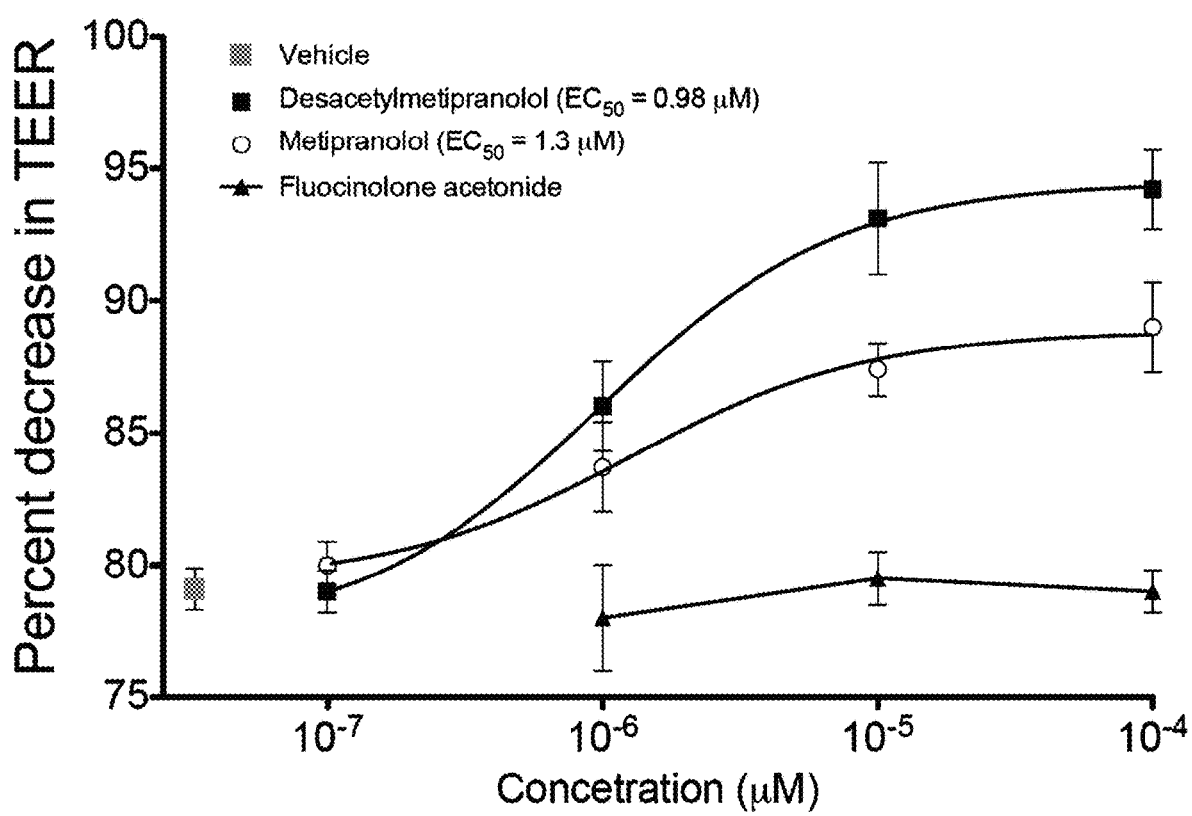
FIG. 3 is a graph of concentration-response curves for desacetylmetipranolol, metipranolol, and fluocinolone inhibition of the reduction of TEER over a time period.

As shown in FIG. 3, suppression of the decrease in TEER induced by gHSA when pretreated with desacetylmetipranolol was concentration-dependent with an EC50=0.98 μM. The suppression of the decrease in TEER induced by gHSA when pretreated with metipranolol was also concentration-dependent with an EC50=1.3 μM. Both metipranolol and desaceytlmetipranol demonstrated suppression of the gHSA induced reduction in RPE resistance. Regression analysis of the concentration response curves also revealed that the concentration response curve had a Hill coefficient not significantly different from 1. No cytotoxicity was observed when using either compound for any of the concentrations tested.

In this study, a third unrelated compound, the corticosteroid fluocinolone acetonide known to reduce edema in humans through transcriptional down regulation of cytokine production including vascular endothelial growth factor, was also evaluated as a positive control for its ability to suppress gHSA-induced reduction in RPE resistance. As shown in FIG. 3, pretreatment with fluocinolone at concentration from $10^{-6}$ to $10^{-4}$ M did not significantly alter the reduction TEER induced by the addition of gHSA (100 μg/mL). No cytotoxicity was observed following the administration of fluocinolone for any of the concentrations tested. AGE is known to exert pathological effects through binding to RAGE receptors which result in increased oxidative stress via upregulation of NADPH oxidase. See Daffu G., Hurtado del Pozo C., O'Shea K M, Ananthakrishnan R., Ravichandran Ramasamy, R., and Schmidt, A. M.; *Radical Roles for RAGE in the Pathogenesis of Oxidative Stress in Cardiovascular Diseases and Beyond; Int. J. Mol. Sci.* 2013, 14, 19891-19910; Rodiño-Janeiro, B. K, Gonzalez-Peteiro, M., Ucieda-Somoza, R., González-Juanatey, Alverez, E.; *Glycated albumin, a precursor of advanced glycation end-products, up-regulates NADPH oxidase and enhances oxidative stress in human endothelial cells: molecular correlate of diabetic vasculopathy; Diabetes Metab Res Rev* 2010; 26: 550-558. Metipranolol and desacetylmetipranolol may be inhibiting the effects of AGE by inhibiting NADPH oxidase.

Example 2

A study investigated the effect of metipranolol on photoreceptor survival and function in rd10$^{+/+}$ mice.

Injections of Metipranolol

Mice were treated in accordance with the Association for Research in Vision and Ophthalmology. Rd10$^{+/+}$ mice (B6.CXB1-Pde6brd10/J) were given daily subcutaneous injections of 40 mg/kg metipranolol provided by the British Pharmacopoeia Commission Laboratory, Tddington, UK or vehicle (PBS containing 5.8% ethanol) between P14 to P65.

Electroretinogram Recordings (ERG)

Scotopic and photopic electroretinograms (ERGs) were recorded using a Diagnosys instrument (Espion, Littleton, Mass.). See Komeima K, Rogers B S, Lu L, Campochiaro P A. *Antioxidants reduce cone cell death in a model of retinitis pigmentosa. Proc Natl Acad Sci USA* 2006; 103:11300-5 and Komeima K, Rogers B S, Campochiaro P A. *Antioxidants slow photoreceptor cell death in mouse models of retinitis pigmentosa. J Cell Physiol* 2007; 213:809-15. For scotopic recordings, rd10 mice were dark adapted for overnight, anesthetized with a mixture of ketamine (100 mg/kg) and xylazine (5 mg/kg) by intraperitoneal injections, and pupils were dilated with 0.5% tropicamide and 0.5% phenylephrine hydrochloride provided by Santen Pharmaceutical Co., Osaka, Japan. Mice were placed on a heating pad and platinum electrodes were placed on the corneas after application of gonioscopic prism solution provided by Alcon Labs, Fort Worth, Tex. Reference electrode was attached subcutaneously between the eyes on the scalp and a ground electrode was attached to the tail. The Ganzfeld illuminator was then placed over the head in a position to ensure equal illumination to both eyes. Scotopic ERGs were recorded at 11 flash intensities (−4, −2.5, −2.2, −1.79, −1.39, −1, −0.6, −0.39, −0.20, 1.0, 1.39 log cd-s/m2). For each flash intensity, 5 readings were taken and averaged. For photopic ERGs, mice were initially light adapted for 7 minutes with 30 cd/m2 background light and flashed at 3 light intensities (0.6, 1.0, 1.39 log cd-s/m2). For each flash intensity, 5 readings were taken and averaged.

Measurement of Outer Nuclear Layer ("ONL") Thickness

Measurements of ONL thickness were performed using methods known to one of skill in the art. See Lee S Y, Usui S, Zafar A B, et al. *N-acetylcysteine promotes long term survival of cones in a model of retinitis pigmentosa.* 2010; 226:1843-9. Briefly, 10 micron frozen ocular sections were cut in the 12:00 to 6:00 meridian, stained with hematoxylin and eosin, visualized with an Axioskop microscope from Zeiss, Thornwood, N.Y. and images were digitized using a three charge-coupled device (CCD) color video camera from Toshiba, Tokyo, Japan, and a frame grabber. Sections through the optic nerve were used to measure ONL thickness at 6 locations: 25% (S1), 50% (S2), and 75% (S3) of the distance between the superior pole and the optic nerve and 25% (I1), 50% (I2), and 75% (I3) of the distance between the inferior pole and the optic nerve. Three separate sections were used for each mouse and averaged. Eight animals injected with vehicle and 9 animals injected with metipranolol were used to evaluate ONL thickness between these two groups.

Measurement of Cone Cell Density

Cone cell density was measured by methods known by one of skill in the arts. See Komeima K, Rogers B S, Lu L, Campochiaro P A. *Antioxidants reduce cone cell death in a model of retinitis pigmentosa. Proc Natl Acad Sci USA* 2006; 103:11300-5 and Komeima K, Rogers B S, Campochiaro P A. *Antioxidants slow photoreceptor cell death in mouse models of retinitis pigmentosa. J Cell Physiol* 2007; 213: 809-15. Briefly, mice at P65 were euthanized and the eyes were removed and fixed in 4% PFA for 1 hour followed by dissection to remove cornea, iris and lens. The retina was carefully isolated from the eyecup and a small incision was made at the nasal position for future orientation. The retinas were incubated in 10% normal goat serum in PBS for 1 hour at room temperature followed by overnight treatment at 4° C. in 1:100 rhodamine-conjugated peanut agglutinin (Vector Laboratories, Burlingame, Calif.) in PBS containing 1% normal goat serum. The retinas were flat mounted and visualized by fluorescence microscopy using an excitation wavelength of 543 nm to detect rhodamine fluorescence of PNA.

The number of cones within four 230 μm×230 μm (512× 512 pixels) squares located 1 mm superior, temporal, inferior, and nasal to the center of the optic nerve were determined.

TUNEL Assay

Apoptotic cells were identified in retinas from P23 mice using the manufacturer's instructions for the In Situ Cell Death Detection Kit (Sigma Aldrich, St. Louis, Mo.).

Nitrite and Nitrotyrosine Assays

Nitrite concentration in retinas from P35 rd10 mice was measured using the Nitrate/Nitrite Colorimetric Assay Kit (Cayman Chemical Company, Ann Arbor, Mich.) according to the manufacturer's instructions. Nitrotyrosine assay was performed on retinas from P35 mice using the 3-Nitrotyrosine ELISA kit (Abcam, Cambridge, Mass.).

Immunohistochemistry

Ten microns ocular frozen sections were stained with anti-rhodopsin antibody 1D4 (1:200, ThermoFisher Scientific, Waltham, Mass.), anti-3-nitrotyrosine antibody (10 μg/ml, EMD Millipore, Temecula, Calif.) or anti-cone arrestin antibody (1:10,000, EMD Millipore, Temecula, Calif.).

Results

Metipranolol Promotes Rod Photoreceptor Survival and Function in P35 rd10 Mice

Figure 4A:
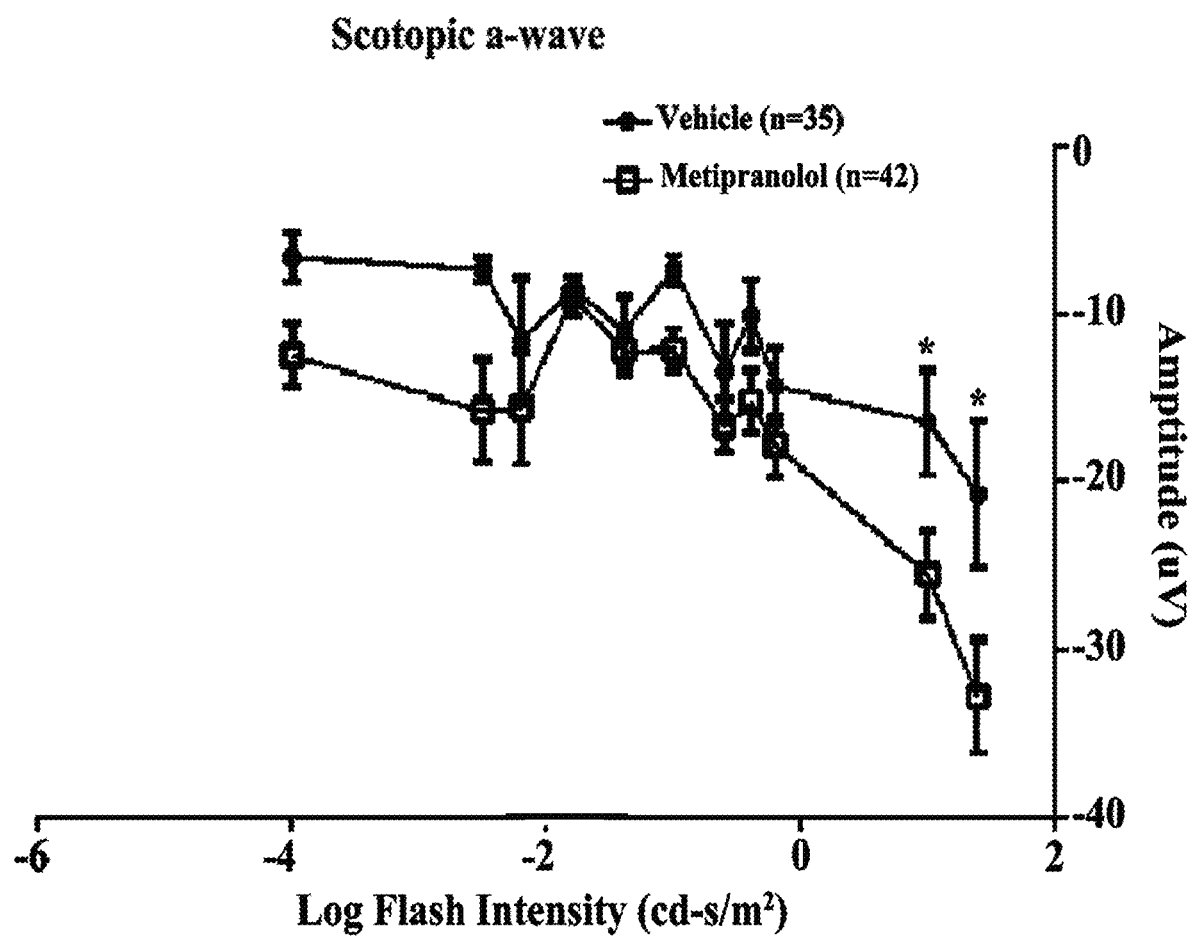
FIG. 4A is a graph showing mean (±SEM) scotopic a-wave amplitude for tested rd10 mice measuring rod photoreceptor survival.
Figure 4B:
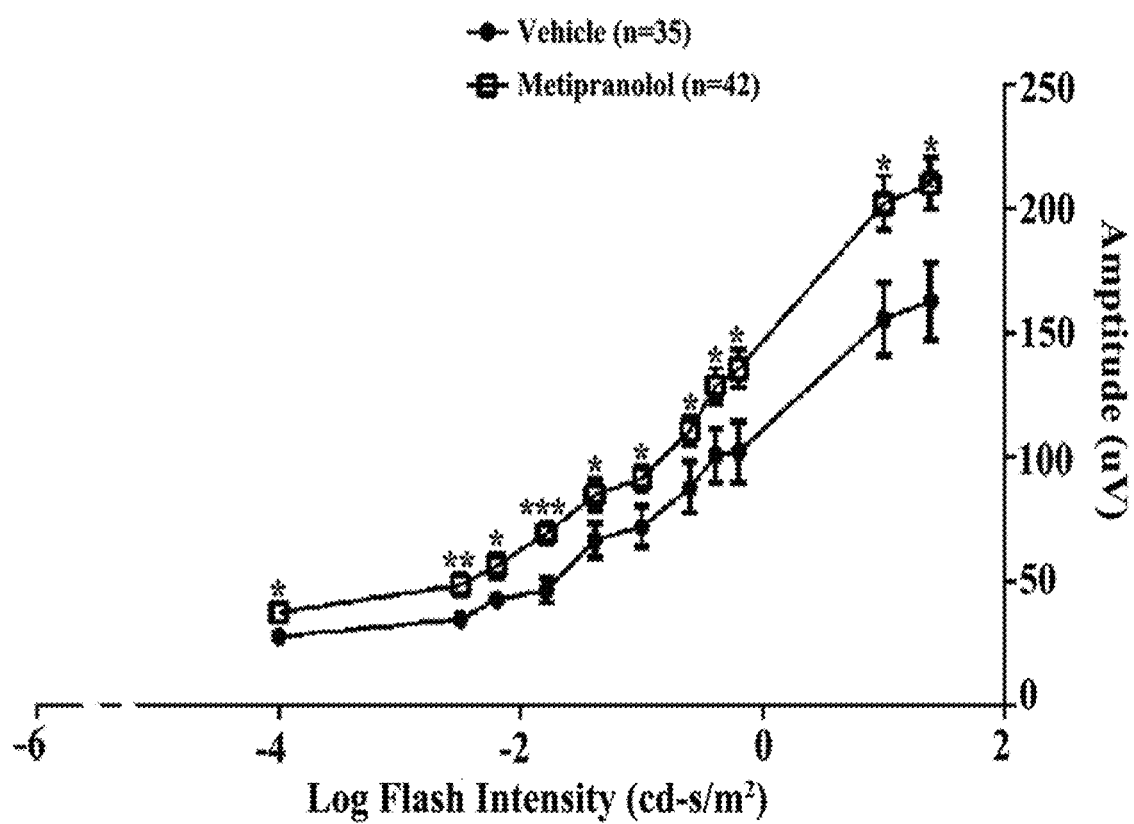
FIG. 4B is a graph showing mean (±SEM) scotopic b-wave amplitude for tested rd10 mice.
Figure 4C:
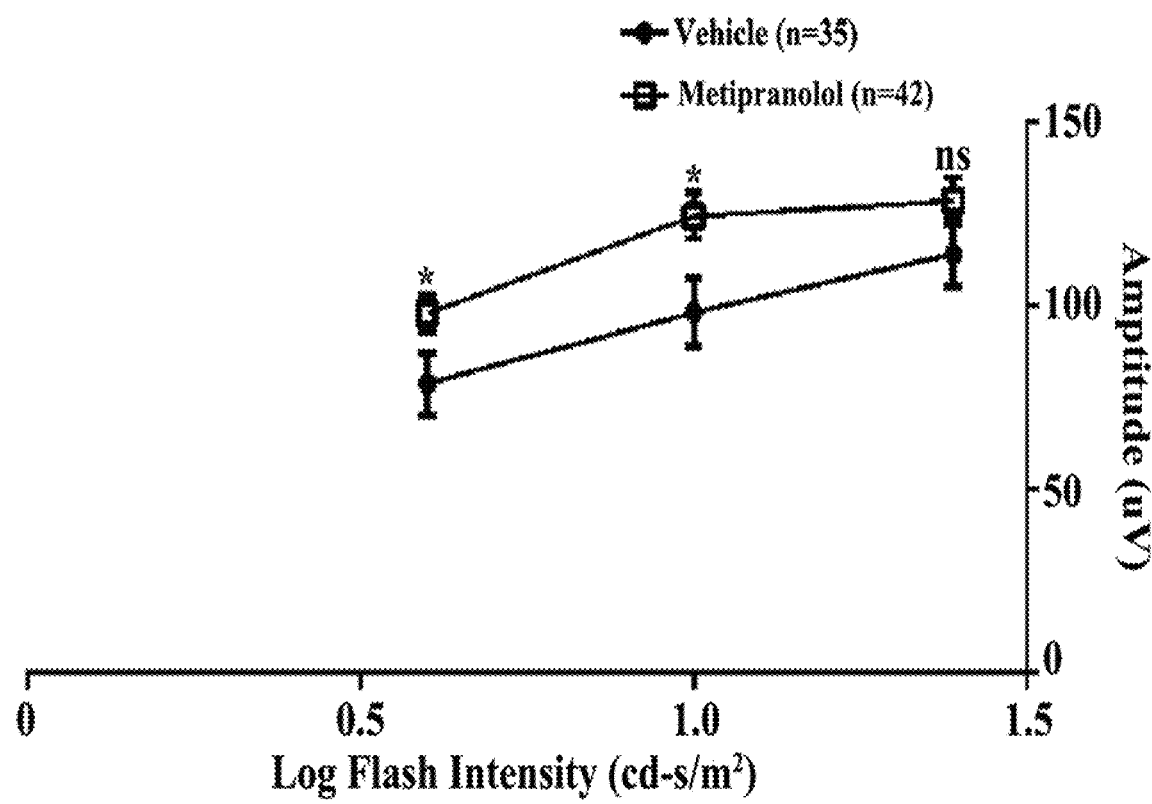
FIG. 4C is a graph showing mean (±SEM) photopic a-wave amplitude for tested rd10 mice.

The peak of rod photoreceptor degeneration in rd10 mice is P25 and most rods have been eliminated by P35. See Chang B, Hawes N L, Hurda R E, et al. *Retinal degeneration* mutants in the mouse. *Vision Res* 2002; 42:517-25; Gargini C, Terzibasi E, Mazzoni F, Strettoi E. *Retinal organization in the retinal degeneration 10 (rd10) mutant mouse: A morphological and ERG study. J Comp Neurol* 2007; 500: 222-38. Starting at P14, rd10 mice were given daily subcutaneous injections of 40 mg/kg metipranolol or vehicle and at P35, mean scotopic a-wave amplitude, which is generated by rod photoreceptors, was significantly greater in metipranolol-treated mice compared with vehicle-treated mice at the two highest flash intensities, 1.0 and 1.39 log cd-s/m2, as shown in FIG. 4A. Mean scotopic b-wave amplitude, which is generated by second order neurons in the rod pathway, was significantly higher in metipranolol-treated mice at all 11 flash intensities, as shown in FIG. 4B. Photopic b-wave amplitudes, which are generated by cone photoreceptors, were significantly higher in metipranolol-treated mice than those treated with vehicle at stimulus intensities of 0.6 and 1.0 log cd-s/m2, as shown in FIG. 4C. These data indicate that metipranolol partially prevented loss of rod and cone photoreceptor function in the rd10 retina at P35.

Figure 4D:
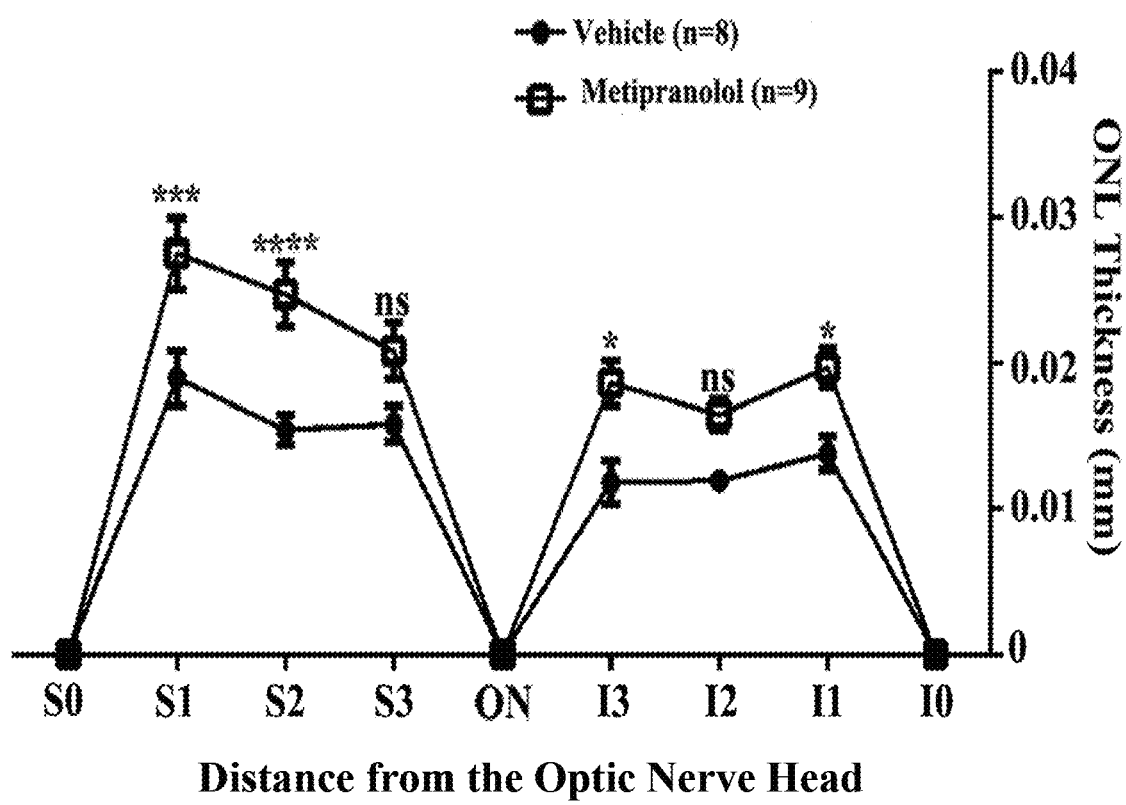
FIG. 4D is a graph showing mean (±SEM) ONL thickness for tested rd10 mice.
Figure 5A:
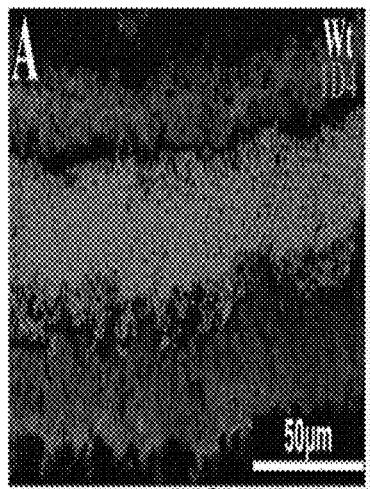
FIG. 5A-5G show results from immunohistochemistry and TUNEL assays of tested rd10 mice.
Figure 5B:
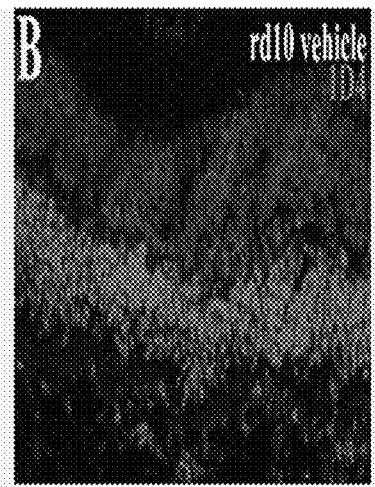
Figure 5C:
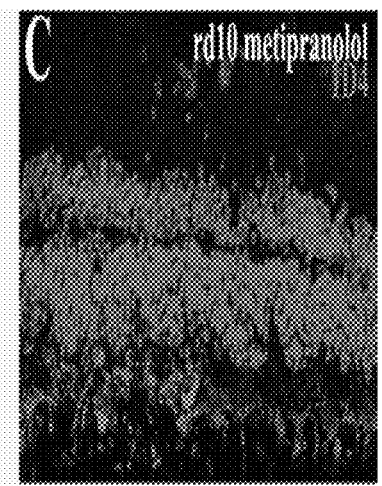
Figure 5D:
Figure 5E:
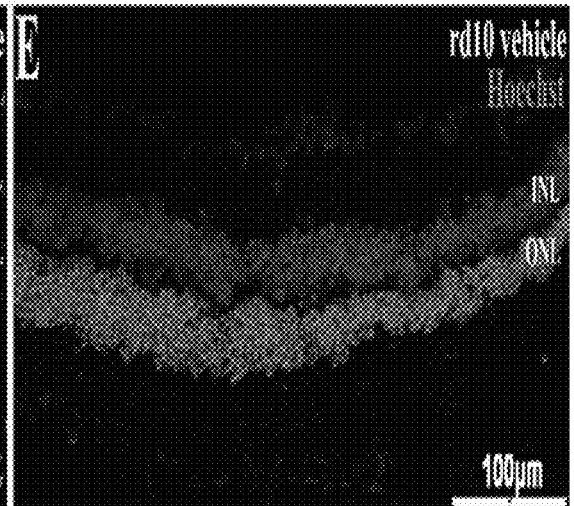
Figure 5F:
Figure 5G:

The thickness of the ONL was measured at 6 locations along the longitudinal meridian of the retina and at P35 mean ONL thickness was significantly greater at 4 of the 6 locations in metipranolol-treated rd10 mice compared to those treated with vehicle (FIG. 4D). Healthy rod photoreceptors transport rhodopsin into outer segments which form a thick band at the outer border of the ONL that intensely immunostains for rhodopsin, as shown in FIG. 5A. Rhodopsin-positive staining was drastically reduced in the outer segments of retinas from vehicle-treated P35 rd10 mice, as shown in FIG. 5B, while there was substantially more rhodopsin staining suggesting surviving outer segments in retinas from metipranolol-treated P35 rd10 mice, as shown in FIG. 5C. Compared to retinas from P23 vehicle-treated rd10 mice which showed numerous TUNEL-positive cells, as shown in FIGS. 5D and 5E by arrows, there were few TUNEL-positive cells in retinas from P23 metipranolol-treated rd10 mice, as shown in FIGS. 5F and 5G.

Metipranolol Promotes Cone Photoreceptor Survival and Function in Rd10 Mice

Figure 6A:
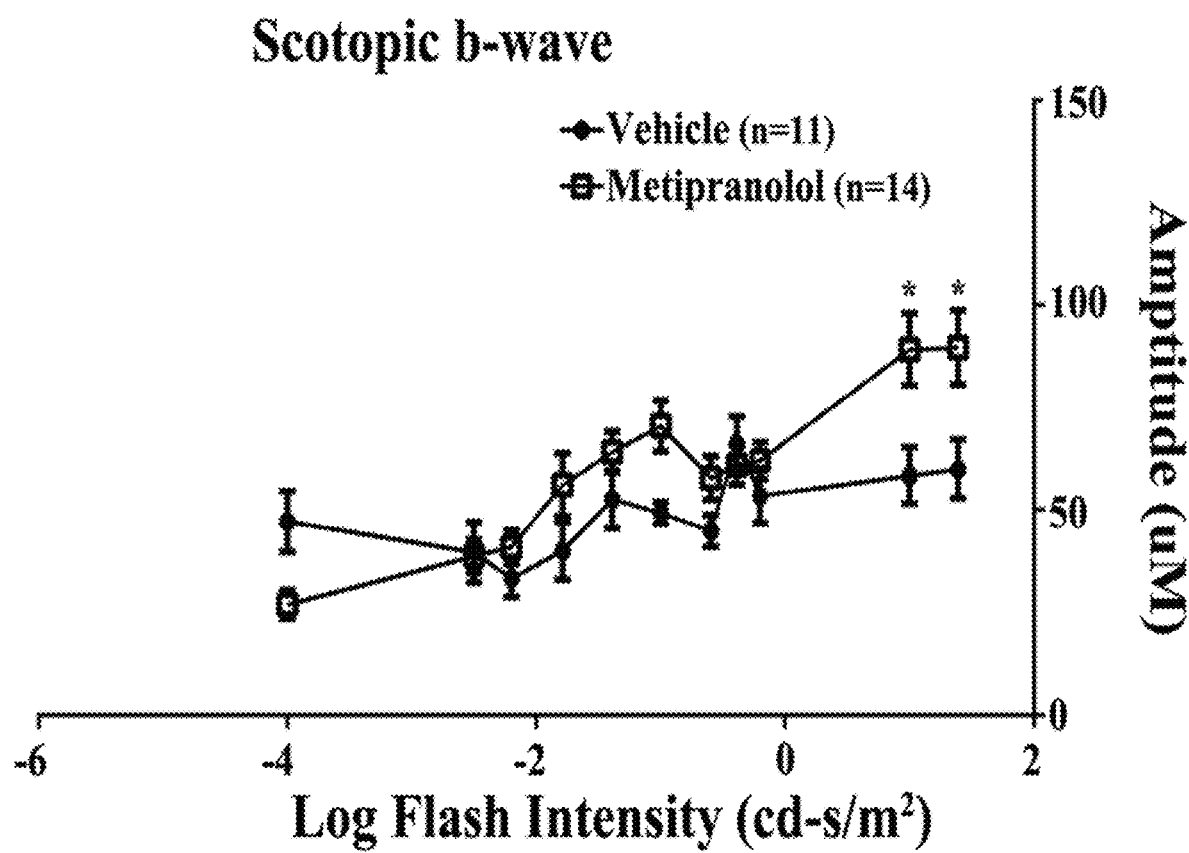
FIG. 6A is a graph showing mean (±SEM) scotopic a-wave amplitude for tested rd10 mice measuring cone photoreceptor survival.
Figure 6B:
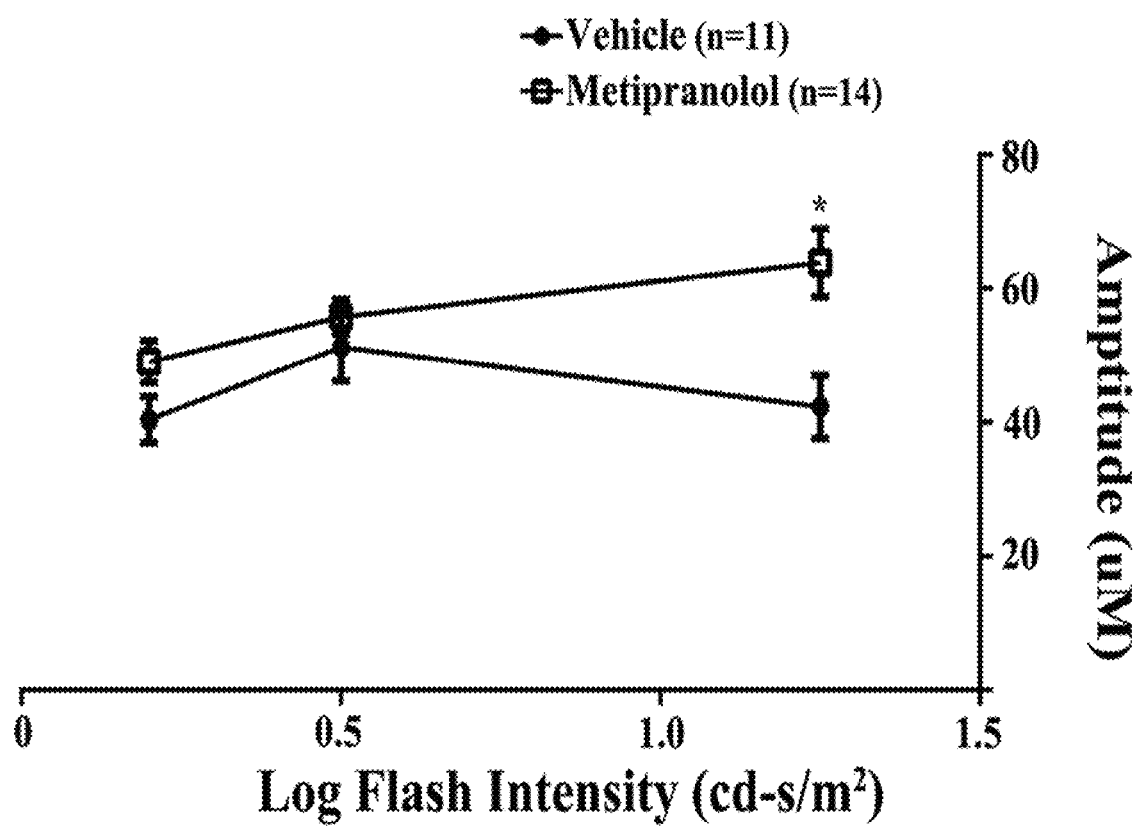
FIG. 6B is a graph showing mean (±SEM) scotopic b-wave amplitude for tested rd10 mice measuring cone photoreceptor survival.
Figure 6C:
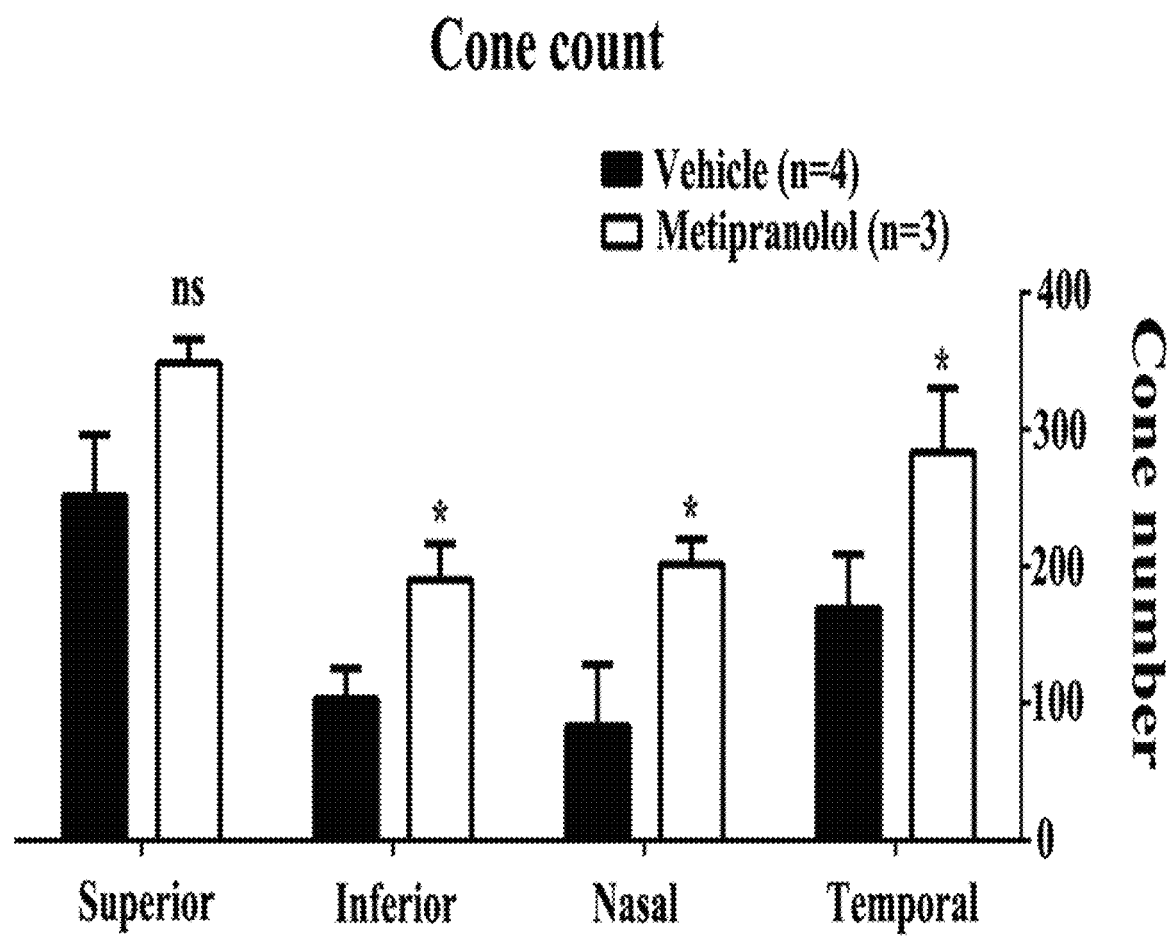
FIG. 6C is a graph showing mean (±SEM) cone cell density for tested rd10 mice.

In rd10 mice, rod degeneration is usually completed by P50 and the ONL consists only of a single layer of cones. See Gargini C, Terzibasi E, Mazzoni F, Strettoi E. *Retinal organization in the retinal degeneration 10 (rd10) mutant mouse: A morphological and ERG study. J Comp Neurol* 2007; 500:222-3. As shown in FIG. 6A, compared with vehicle-treated P50 rd10 mice, those treated with metipranolol had significantly higher mean scotopic b-wave amplitude at flash intensities of 1.0 and 1.39 log cd-s/m2. Mean photopic b-wave amplitude was significantly greater in metipranolol-treated mice at the highest flash intensity of 1.39 log cd-s/m2, as shown in FIG. 6B. FIG. 6C shows that at P65, mean cone photoreceptor cell density was significantly greater in 3 of 4 quadrants of metipranolol-treated rd10 mice compared with vehicle-treated mice.

Figure 7A:
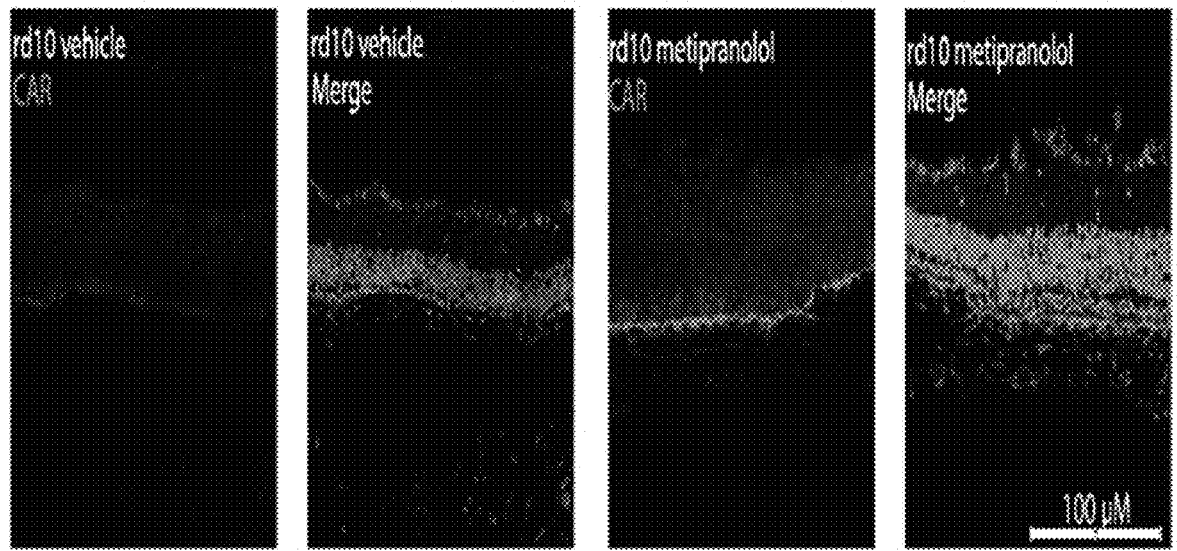
FIGS. 7A-7D show results of cone arrestin and attenuated nitric oxide stress for tested rd10 mice.
Figure 7B:
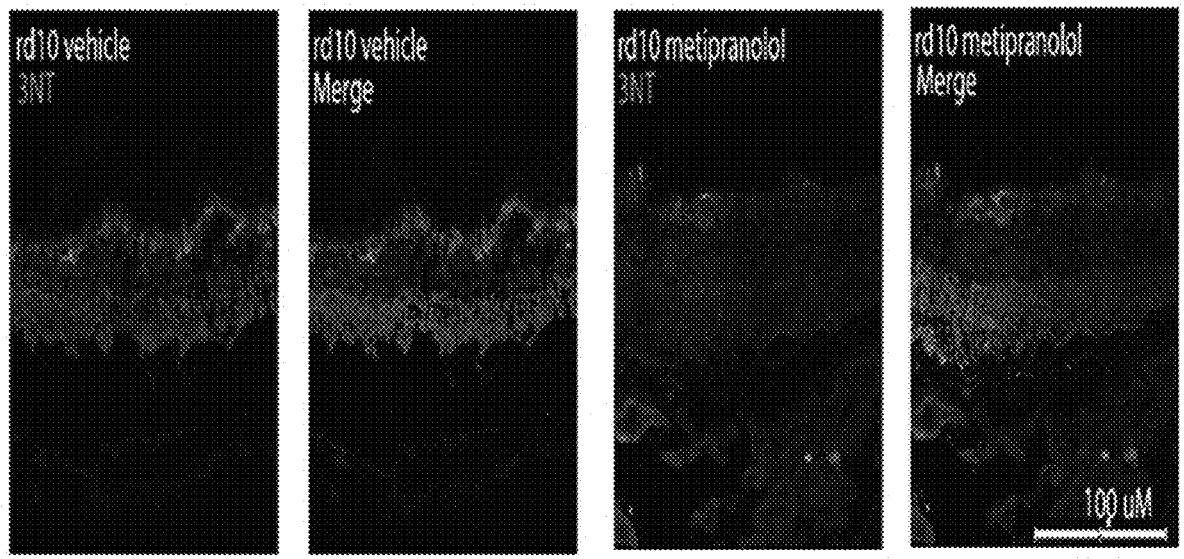
Figure 7C:
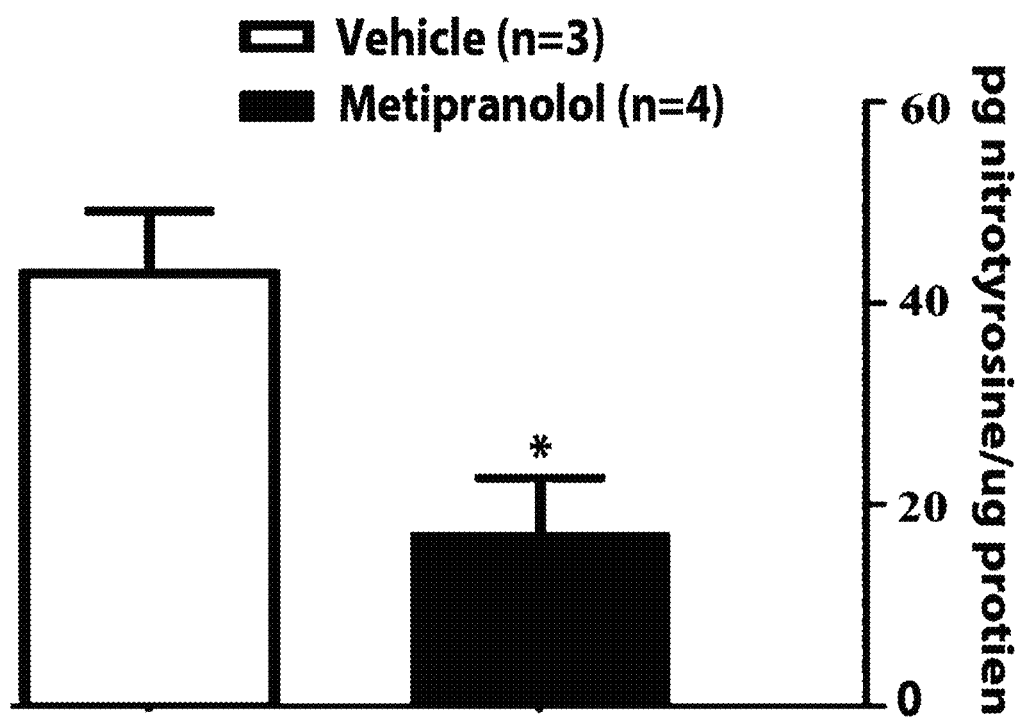

In FIG. 7A, the left panel shows that immunostaining for cone arrestin, an essential protein in the cone visual transduction cascade, was nearly undetectable in vehicle-treated P50 rd10 mice, it was hard to discern an ONL, and the inner nuclear layer was thin. In contrast, the right panel of FIG. 7A demonstrates that at the same location in retinas from metipranolol-treated P50 rd10 mice, staining for cone arrestin was robust, an ONL consisting of a couple rows of cells could be discerned, and the inner nuclear layer was thicker than that seen in vehicle-treated mice. Turning to FIG. 7B, the left panel of the figures shows that there was greater staining for nitrotyrosine in retinas from P50 vehicle-treated rd10 mice, than in P50 metipranolol-treated rd10 mice, as shown in the right panel of the figure. The nitrotyrosine staining was visible in vehicle injected rd10 mice at P35, albeit highly reduced compared to P50 (data not shown). However, as shown in FIG. 7C, nitrotyrosine ELISA showed that, compared with vehicle-treated retinas from P35 rd10 mice, there was a significant reduction in mean concentration of 3-nitrotyrosine protein adducts in retinas from P35 metipranolol-treated rd10 mice.

Figure 7D:
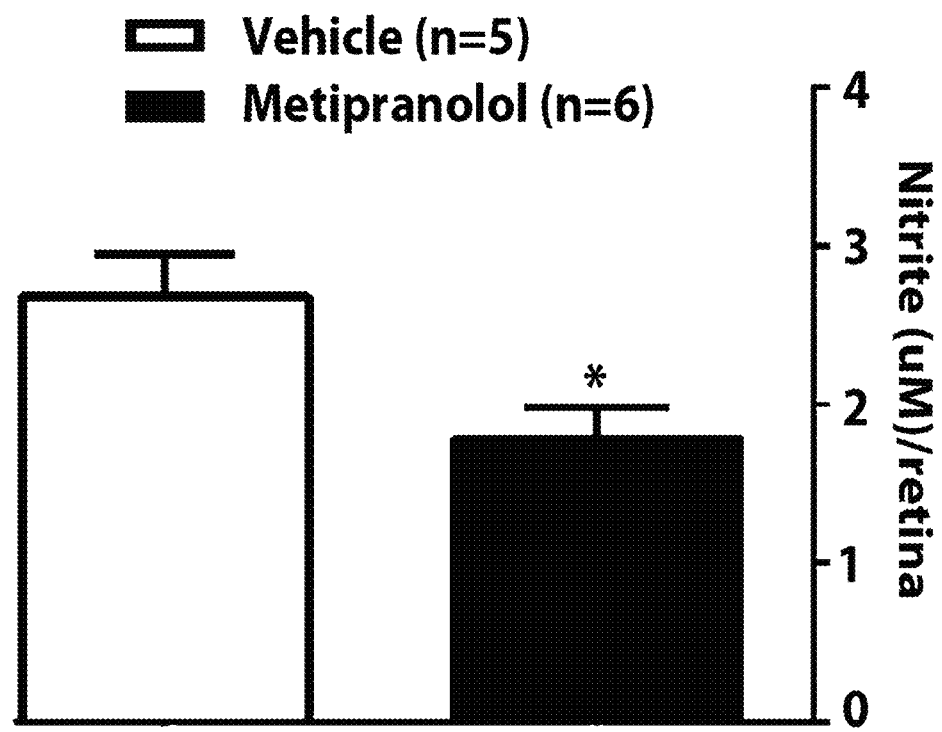

The mean concentration of nitrite, another marker of nitosative damage (see van't Hof R J, Ralston S H. *Nitric oxide and bone. Immunology* 2001; 103(3):255-61) was also significantly greater in retinal homogenates from P35 vehicle-treated versus metipranolol-treated rd10 mice (FIG. 7D). Superoxide radicals were also evaluated by using the superoxide indicator dihydroethidium dye and no differences were found between vehicle and metipranolol injected retinas (data not shown). The anti-nitrosative damage activity of metipranolol is not mediated by suppression of NADPH Oxidase because metipranolol did not reduce NADPH Oxidase activity in retinas of rd10 mice. These data suggest that metipranolol has no effect on generation of superoxide radicals in the retinas of rd10 mice and instead acts downstream to reduce generation of peroxynitrite.

Example 3

A study investigated the effect of metipranolol on choroidal neovascularization.

Choroidal Neovascularization

Choroidal neovascularization was induced by methods known to one of ordinary skill in the art. See Tobe T, Ortega S, Luna J D, et al. *Targeted disruption of the FGF2 gene does not prevent choroidal neovascularization in a murine model. Am J Pathol* 1998; 153(5):1641-6. Adult C57bl/6 female mice (Charles River, Wilmington, Mass.), 5 weeks of age, were given daily subcutaneous injections of 40 mg/kg metipranolol or vehicle (PBS containing 5.8% ethanol) every day, starting 3 days before laser-induced Bruch's membrane rupture and continuing through 1 week after laser treatment. Mice were anesthetized, with a mixture of ketamine (100 mg/kg) and xylazine (5 mg/kg) by intraperitoneal injections, and pupils were dilated with 0.5% tropicamide and 0.5% phenylephrine hydrochloride from Santen Pharmaceutical Co., Osaka, Japan. Three laser burns using 532-nm diode laser (75-µm spot size, 0.1-s duration, 140 mW) were delivered to both retinas using the slit-lamp delivery system of an OcuLight GL Photocoagulator (Iridex, Mountain View, Calif.) and a hand-held cover slide as contact lens. Burns were performed in the 12, 3 and 6-o'clock positions of the posterior pole of the retina. Following 1 week after laser, animals were euthanized and choroidal neovascularization was measured. Eyes were dissected to remove cornea, lens and retina. The remaining eyecups consisting of the retinal pigmented epithelium, choroid, and sclera were stained with FITC-labeled Griffonia Simplicifolia lectin (GSA), which selectively stains vascular cells, fluorescent images were captured with an Axioskop microscope from Zeiss, Thornwood, N.Y., and the area of choroidal neovascularization at Bruch's membrane rupture sites were measured. These images were quantified using Image-Pro Plus software. The three values from a single eye were averaged to give a single experimental value and the mean area of choroidal neovascularization in the metipranolol-injected experimental group and the vehicle-injected control group were compared using unpaired two tailed t-test using GraphPad Prism software (San Diego, Calif.).

Results

Metipranolol Suppresses Choroidal Neovascularization

Figure 8A:
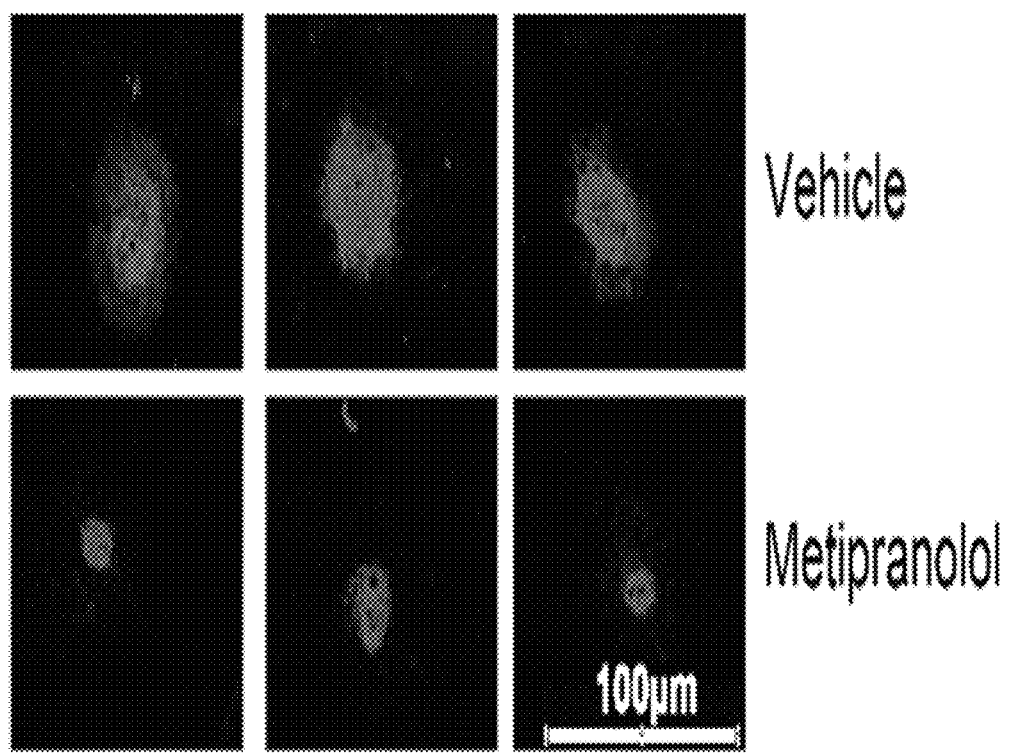
FIG. 8A shows images of GSA-stained blood vessel for tested rd10 mice.
Figure 8B:
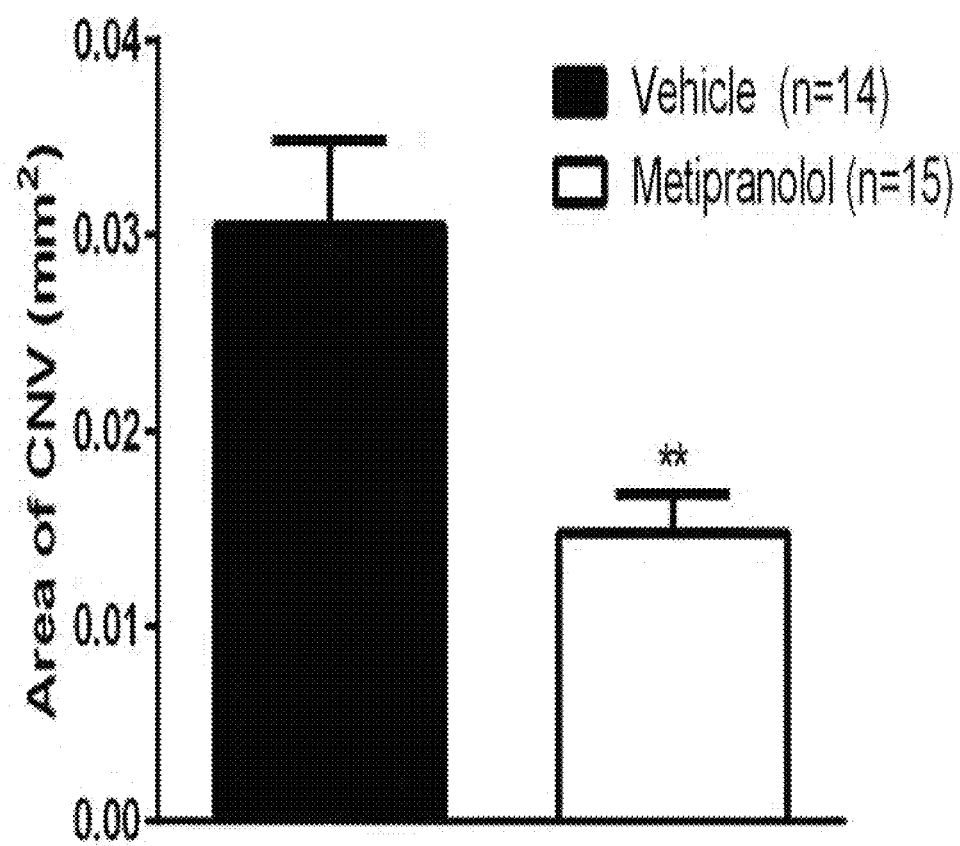
FIG. 8B shows quantification of mean area of CNV for tested rd10 mice.

It has been previously been shown that oxidative or nitrosative damage exacerbates choroidal neovascularization. See Ando A, Mori K, Yamada H, et al. *Nitric oxide is proangiogenic in retina and choroid. J Cell Physiol* 2002; 191:116-24; Dong A, Xie B, Shen J, et al. *Oxidative stress promotes ocular neovascularization. J Cell Physiol* 2009; 219:544-52; and Dong A, Shen J, Zeng M Campochiaro P A. *Vascular cell adhesion molecule-1 plays a central role in the proangiogenic effects of oxidative stress. Proc Natl Acad Sci USA* 2011; 108:14614-9. As demonstrated by FIGS. 8A and 8B, this study found that compared to vehicle-treated control mice, the area of choroidal neovascularization at Bruch's membrane rupture sites was significantly reduced in metipranolol-treated mice.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention.

The invention claimed is:

1. A method of treating or inhibiting degeneration of a retina of a subject in need thereof comprising administering a dosage of an effective amount of desacetylmetipranolol to the eye of the subject, wherein the degeneration of the retina is caused by an ocular disease selected from the group consisting of diabetic retinopathy and choroidal neovascularization, wherein the dosage of the effective amount of desacetylmetipranolol is administered parenterally to the eye of the subject by direct injection.

2. The method of claim 1, wherein the dosage of the effective amount of desacetylmetipranolol is within a drug delivery vehicle comprising biocompatible polymers or copolymers configured to release the effective amount of desacetylmetipranolol in a controlled manner and wherein the drug delivery vehicle is delivered via intravitreal injection.

3. The method of claim 2, wherein the dosage of the effective amount of desacetylmetipranolol of the drug delivery vehicle ranges from 0.5 µg/day to 15 µg/day.

4. The method of claim 2, wherein the drug delivery vehicle is bioerodible.

5. The method of claim 2, wherein the drug delivery vehicle is an intravitreal insert.

6. The method of claim 2, wherein the drug delivery vehicle is an amorphous mass.

7. A method of treating or inhibiting dystrophy of rods and cones of a retina of a subject in need thereof comprising administering a dosage of an effective amount of desacetylmetipranolol to the eye of the subject.

8. The method of claim 7, wherein the dosage of the effective amount of desacetylmetipranolol is within a drug delivery vehicle comprising biocompatible polymers or copolymers configured to release the effective amount of desacetylmetipranolol in a controlled manner and wherein the drug delivery vehicle is delivered via intravitreal injection.

9. The method of claim 7, wherein the dosage of the effective amount of desacetylmetipranolol of the drug delivery vehicle ranges from 0.5 µg/day-15 µg/day.

10. The method of claim 7, wherein the drug delivery vehicle is bioerodible.

11. The method of claim 7, wherein the drug delivery vehicle is an intravitreal insert.

12. The method of claim 7, wherein the drug delivery vehicle is an amorphous mass.

* * * * *